United States Patent
Zuk et al.

(10) Patent No.: US 10,809,251 B2
(45) Date of Patent: Oct. 20, 2020

(54) IMMUNOASSAY WITH ENHANCED SENSITIVITY

(71) Applicant: ACCESS MEDICAL SYSTEMS, LTD., Palo Alto, CA (US)

(72) Inventors: Robert F. Zuk, Menlo Park, CA (US); Hong Tan, San Jose, CA (US); Qing Xia, Sunnyvale, CA (US); Pu Li, San Jose, CA (US); Haode Chen, Shanghai (CN); Heng Wu, Shanghai (CN)

(73) Assignee: ACCESS MEDICAL SYSTEMS, LTD., Palo Alto, CA (US)

( * ) Notice: Subject to any disclaimer, the term of this patent is extended or adjusted under 35 U.S.C. 154(b) by 224 days.

(21) Appl. No.: 15/903,838

(22) Filed: Feb. 23, 2018

(65) Prior Publication Data

US 2018/0180606 A1    Jun. 28, 2018

Related U.S. Application Data

(63) Continuation of application No. PCT/US2016/048672, filed on Aug. 25, 2018.
(Continued)

(51) Int. Cl.
  *G01N 33/543*    (2006.01)
  *G01N 33/533*    (2006.01)
  (Continued)

(52) U.S. Cl.
  CPC ....... *G01N 33/54306* (2013.01); *G01N 33/53* (2013.01); *G01N 33/533* (2013.01);
  (Continued)

(58) Field of Classification Search
  CPC .. G01N 33/53; G01N 33/5306; G01N 33/533; G01N 33/543; G01N 33/54306; G01N 33/582
  (Continued)

(56) References Cited

U.S. PATENT DOCUMENTS 5,494,830 A * 2/1996 Hubscher ........... G01N 33/5302
                                                      422/404
8,492,139 B2   7/2013 Tan et al.
(Continued)

FOREIGN PATENT DOCUMENTS

CA    2519903 C    9/2005
WO    2010101931 A2   9/2010
WO    2013158494 A1   10/2013

OTHER PUBLICATIONS

International Search Report dated Dec. 8, 2016 of PCT/US2016/048672 (2 pages).
(Continued)

*Primary Examiner* — Christopher L Chin
(74) *Attorney, Agent, or Firm* — Perkins Coie LLP; Viola Kung (57) ABSTRACT

The present invention is directed to methods for increasing sensitivities of immunoassays. The invention utilizes an acid elution condition that preferentially elute specifically bound immune complexes over non-specifically bound complexes from a solid phase, and designs immunoassay protocols that improve the ratio of specific binding to non-specific binding and thereby improving assay sensitivity. The protocol determines the signal of the labeled immunocomplexes eluted from a solid phase.

14 Claims, 6 Drawing Sheets

Related U.S. Application Data (60) Provisional application No. 62/210,372, filed on Aug. 26, 2015.

(51) Int. Cl.
   *G01N 33/53* (2006.01)
   *G01N 33/58* (2006.01)

(52) U.S. Cl.
   CPC ....... *G01N 33/5306* (2013.01); *G01N 33/543* (2013.01); *G01N 33/582* (2013.01)

(58) Field of Classification Search
   USPC .......................................................... 436/809
   See application file for complete search history.

(56) References Cited

U.S. PATENT DOCUMENTS

| | | |
|---|---|---|
| 8,647,889 B2 | 2/2014 | Zuk et al. |
| 9,568,431 B2 | 2/2017 | Zuk |
| 2009/0023144 A1 | 1/2009 | Sun |

OTHER PUBLICATIONS

Edward J. Wild et al., "Quantification of mutant huntingtin protein in cerebrospinal fluid from Huntington's disease patients", Journal of Clinical Investigation, Apr. 6, 2015, vol. 125, No. 5, pp. 1979-1986.

Joseph Barco, "Conversion of ELISA to SMC™ Technology: Advanced Platform Designed to Provide 1,000-Fold Improved Quantification", Genetic Engineering & Biotechnology News, Dec. 1, 2014, vol. 34, No. 21, pp. 16-17.

Saloumeh K. Fischer, et al., "Emerging Technologies to Increase Ligand Binding Assay Sensitivity", The AAPS Journal, Oct. 18, 2014, vol. 17, No. 1, pp. 93-101.

Supplementary European Search Report dated Jan. 25, 2019 issued in EP 16840112.

\* cited by examiner hs TnI Designation: Based On Normals

| Acceptance Designation | Imprecision at 99th % |
|---|---|
| Giudeline Acceptable | </= 10% CV |
| Clinically Usable | >10 - </=20% CV |
| Not acceptable | >20% CV |
| Assay Designation | Measurable Normal Values |
| 3rd Gen | >/= 95% |
| 2nd Gen | 75-95% |
| 1st Gen | 50 - 75% |
| Contemporary | <50% |

FIG. 1

Types of Solid Phase Binding

Immuno-Specific Binding

Solid Phase  -AB: AG : AB-Label

Non-Specific Binding

-AB

AB-Label

IMMUNOASSAY WITH ENHANCED SENSITIVITY

This application is a continuation of PCT/US2016/048672, filed Aug. 25, 2016; which claims the benefit of U.S. Provisional Application No. 62/210,372, filed Aug. 26, 2015. The contents of the above-identified applications are incorporated herein by reference in their entirety.

BACKGROUND OF THE INVENTION

Improving immunoassay sensitivity has been a longstanding goal in development of in vitro diagnostic tests. The benefits of sensitive biomarker measurements for early disease detection and cost effectiveness in patient triage are well documented. Over time many clinical assays have been offered in several generations where each subsequent iteration features improved sensitivity. Troponin I immunoassays are one such example where high sensitivity versions represent the state of the art.

Figure 1:
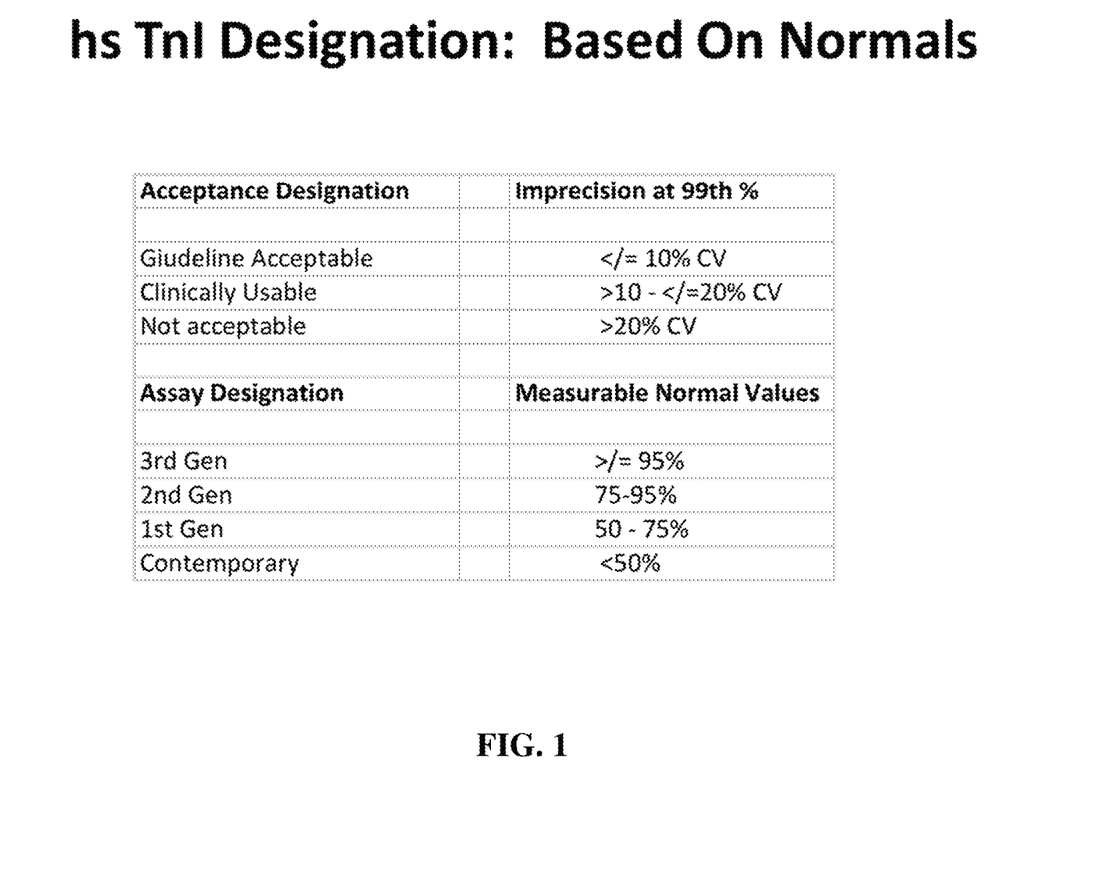
FIG. 1 shows the parameters that highly sensitive troponin I (hsTnI) must meet based on normal.

Several clinical factors are responsible for driving the adoption of highly sensitive troponin I (hsTnI) assays. There is recognition that normal patients have circulating, low levels of TnI in the range of single digit pg/ml. Secondly, small heart attacks have TnI levels very similar to normal. Consequently, the ability to detect TnI within the normal range is critical. Apple (Clin. Chem., 55: 1303-1306, 2009) reports the designation of hsTnI assays centering on performance with normal samples. FIG. 1 shows the parameters that hsTnI assays must meet. Greater than 50% of normal must be detected and imprecision at the $99^{th}$ percentile of the normal distribution must be <10% to be guideline acceptable or 10-20% to be clinically useful.

Figure 2:
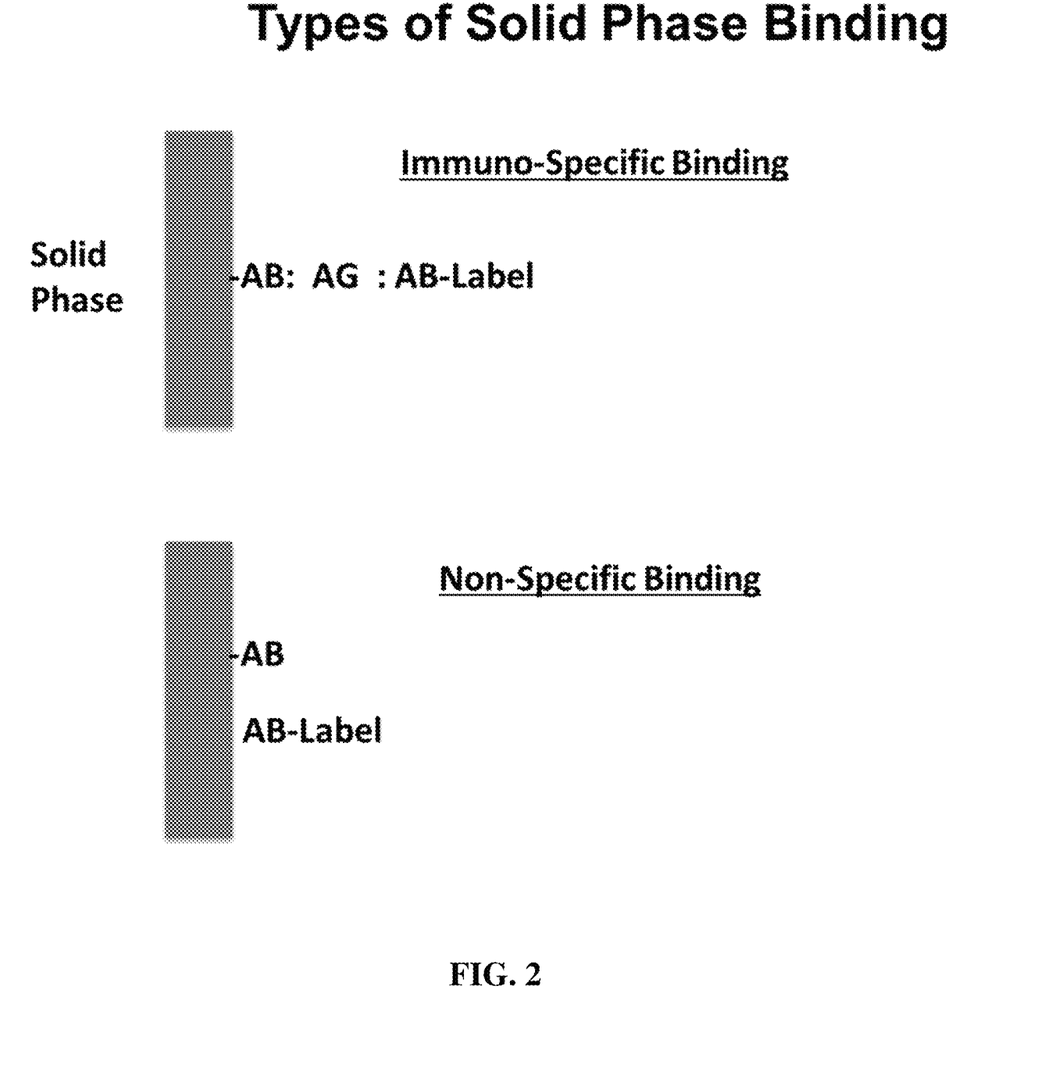
FIG. 2 illustrates a typical solid phase sandwich immunoassay format. AB=antibody, AG=antigen.

FIG. 2 illustrates a typical sandwich immunoassay format with a capture antibody and a labeled antibody, where the capture antibody is immobilized on a solid phase. There are two basic types of binding by the labeled antibody. Immunospecific binding occurs when the labeled antibody forms a complex with antigen on the solid phase. This is the relevant specific binding since it enables antigen detection. The second type of binding is non-specific where the labeled antibody binds to the solid phase by means other than the specific antigen. Every solid phase configured sandwich immunoassay has some combination of specific versus non-specific binding. With high sensitivity immunoassays the ratio of specific to non-specific binding becomes crucial at low antigens levels. Consequently, developers of high sensitivity assays strive to maximize specific binding while seeking means to minimize non-specific binding.

BRIEF DESCRIPTION OF THE DRAWINGS

FIG. 7 illustrates a method of detecting an analyte in a liquid sample in a cyclic amplification assay. FIG. 7 is similar to FIG. 6, except FIG. 7 has additional cyclic amplification steps to improve sensitivity.

DETAILED DESCRIPTION OF THE INVENTION

Definitions

Terms used in the claims and specification are to be construed in accordance with their usual meaning as understood by one skilled in the art except and as defined as set forth below.

"About," as used herein, refers to within ±10% of the recited value.

An "analyte-binding" molecule, as used herein, refers to any molecule capable of participating in a specific binding reaction with an analyte molecule. Examples include but are not limited to, (i) antigen molecules, for use in detecting the presence of antibodies specific against that antigen; (ii) antibody molecules, for use in detecting the presence of antigens; (iii) protein molecules, for use in detecting the presence of a binding partner for that protein; (iv) ligands, for use in detecting the presence of a binding partner; or (v) single stranded nucleic acid molecules, for detecting the presence of nucleic acid binding molecules.

An "aspect ratio" of a shape refers to the ratio of its longer dimension to its shorter dimension.

A "binding molecular," refers to a molecule that is capable to bind another molecule of interest.

"A binding pair," as used herein, refers to two molecules that are attracted to each other and specifically bind to each other. Examples of binding pairs include, but not limited to, an antigen and an antibody against the antigen, a ligand and its receptor, complementary strands of nucleic acids, biotin and avidin, biotin and streptavidin, biotin and neutravidin (a deglycosylated version of avidin), lectin and carbohydrates. Preferred binding pairs are biotin and streptavidin, biotin and avidin, biotin and neutravidin, fluorescein and anti-fluorescein, digioxigenin/anti-digioxigenin, and DNP (dinitrophenol) and anti-DNP.

A "branched polymer," as used herein, refers to a non-linear polymer having a 2- or 3-dimensional structure, which can be either a naturally occurring branched polymer, or a synthetically crosslinked polymer.

"Chemiluminescence," as used herein, refers to the emission of energy with limited emission of luminescence, as the result of a chemical reaction. For example, when luminol reacts with hydrogen peroxide in the presence of a suitable catalyst, it produces 3-aminophthalate in an excited state, which emits light when it decays to a lower energy level.

"Electrochemiluminescence," (ECL), as used herein, refers to luminescence produced during electrochemical reactions in solutions. In ECL, electrochemically generated intermediates undergo a highly exergonic reaction to produce an electronically excited state and then emits light. ECL excitation is caused by energetic electron transfer (redox) reactions of electrogenerated species. ECL is usually observed during application of potential (several volts) to electrodes of electrochemical cell that contains solution of luminescent species.

"Immobilized," as used herein, refers to reagents being fixed to a solid surface. When a reagent is immobilized to a solid surface, it is either be non-covalently bound or covalently bound to the surface.

"A monolithic substrate," as used herein, refers to a single piece of a solid material such as glass, quartz, or plastic that has one refractive index.

A "probe," as used herein, refers to a solid phase substrate coated with a thin-film layer of analyte-binding molecules at the sensing side. A probe has a distal end and a proximal end. The proximal end (also refers to probe tip in the application) has a sensing surface coated with a thin layer of analyte-binding molecules.

The present invention relates to a method to increase signal to background ratio in an immunoassay and thus increasing the assay sensitivity. The inventors have discovered that conditions to elute specific immune complexes from a solid phase are different from conditions to elute non-specific complexes. The inventors have discovered elution conditions that preferentially elute specific immune complexes over non-specific complexes from a solid phase, and then designed immunoassay protocols that improve the measured ratio of specific binding to non-specific binding and thereby improving assay sensitivity. This invention detects an analyte by determining the signals of the labeled immunocomplex eluted from a solid phase, after it is bound on a solid phase.

Fluorescent Detection System

The present invention may use any suitable luminescent detection system. In one embodiment, the present invention uses a fluorescent detection system similar to that described in U.S. Pat. No. 8,492,139, which is incorporated herein by reference in its entirety, for measuring a fluorescent signal on a probe tip. The system comprises: (a) a probe having an aspect ratio of length to width at least 5 to 1, the probe having a first end and a second end, the second end having a sensing surface bound with a fluorescent label; (b) a light source for emitting excitation light directly to the probe's sensing surface; (c) a collecting lens pointed toward the sensing surface; and (d) an optical detector for detecting the emission fluorescent light; where the collecting lens collects and directs the emission fluorescent light to the optical detector.

The probe can be a monolithic substrate or an optical fiber. The probe can be any shape such as rod, cylindrical, round, square, triangle, etc., with an aspect ratio of length to width of at least 5 to 1, preferably 10 to 1. Because the probe is dipped in a sample solution and one or more assay solutions during an immunoassay, it is desirable to have a long probe with an aspect ratio of at least 5 to 1 to enable the probe tip's immersion into the solutions. The sensing surface of the probe is coated with analyte-binding molecules and bound with fluorescent labels.

Any light source that can emit proper excitation light for the fluorescent label is suitable for the present invention. A prefer light source is a laser that can emit light with wavelengths suitable for fluorescent labels. For example, the laser center wavelength is preferred to be 649 nm for Cy5 fluorescent dye. A suitable optical detector for detecting emission light is a photomultiplier tube (PMT), a charge coupled device (CCD), or a photodiode.

The light source and the optical detector including collecting lens are mounted on the same side of the probe tip surface (the sensing surface). If the sensing surface faces down, they are both mounted below the tip surface. If the sensing surface faces up, they are both mounted above the tip surface. They are closer to the sensing surface than the other end of the probe. The sensing surface is always within the numeric aperture of the collecting lens. The probe can be, but does not have to be centrally aligned with the collecting lens.

Figure 3:
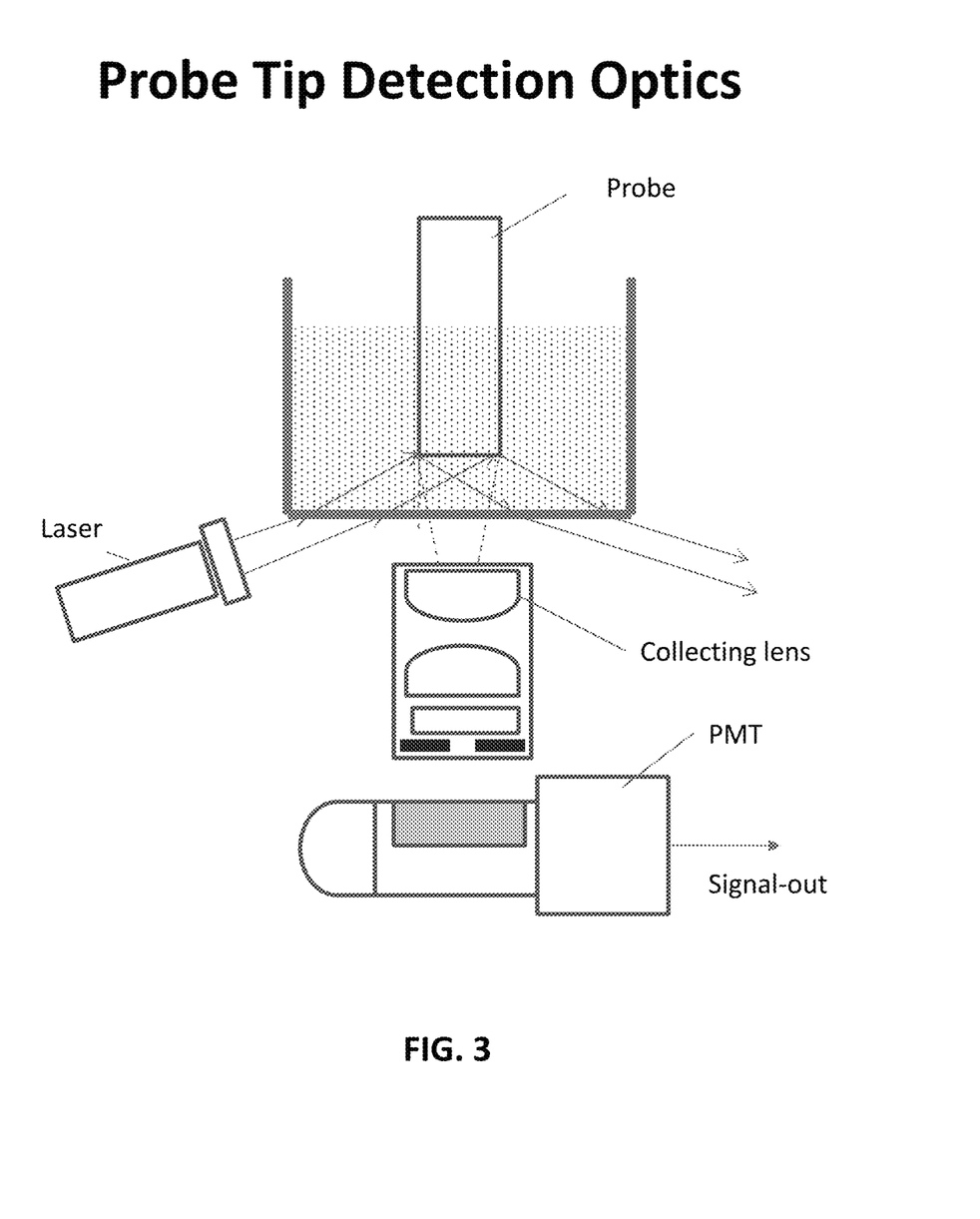
FIG. 3 illustrate one embodiment of the fluorescent detection system, which detects the fluorescence on the probe tip.

FIG. 3 illustrate one embodiment of the fluorescent detection system which measures the fluorescent signals on the probe tip.

Figure 4:
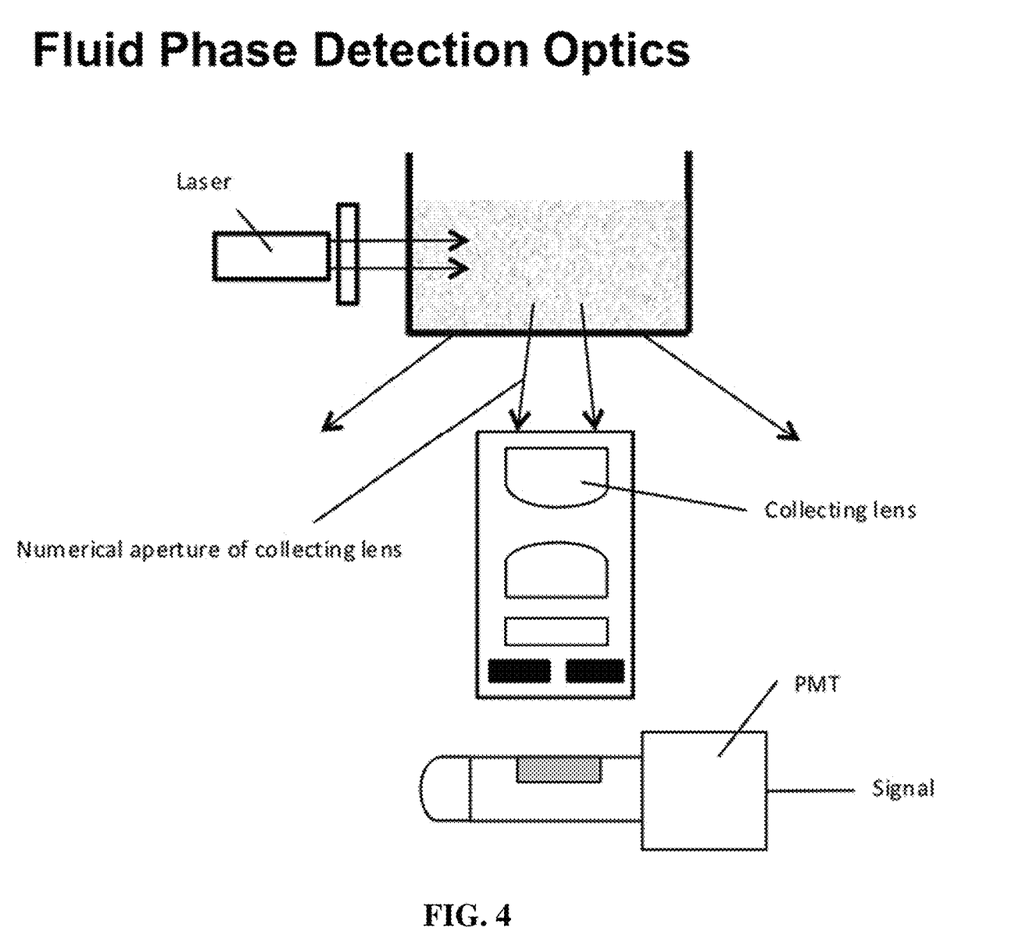
FIG. 4 illustrates an alternative fluorescent detection system. The optics with a wide laser beam and numerical aperture of the collecting lens detect the eluted labeled antibody in a liquid phase.

FIG. 4 illustrates an alternative optical detection configuration. The optics with a wide laser beam and numerical aperture of the collecting lens detect the eluted labeled antibody in fluid phase. This design has several advantages. Measurement of fluorescence at the probe tip demands selection of probe material with low background fluorescence. In this alternative configuration, the fluorescence is in the liquid phase. Since the probe is no longer in the measurement step, it provides a greater selection of solid phase material for the probe. Further, the wide beam laser and broad field of fluorescence collection require less critical alignment of the optics, which leads to lower cost and more robust instrumentation.

Direct Antibody Binding Assay

In a first aspect, the present invention is directed to a method of detecting an analyte in a liquid sample, using luminescent-labeled antibody and acid elution protocols.

Figure 5:
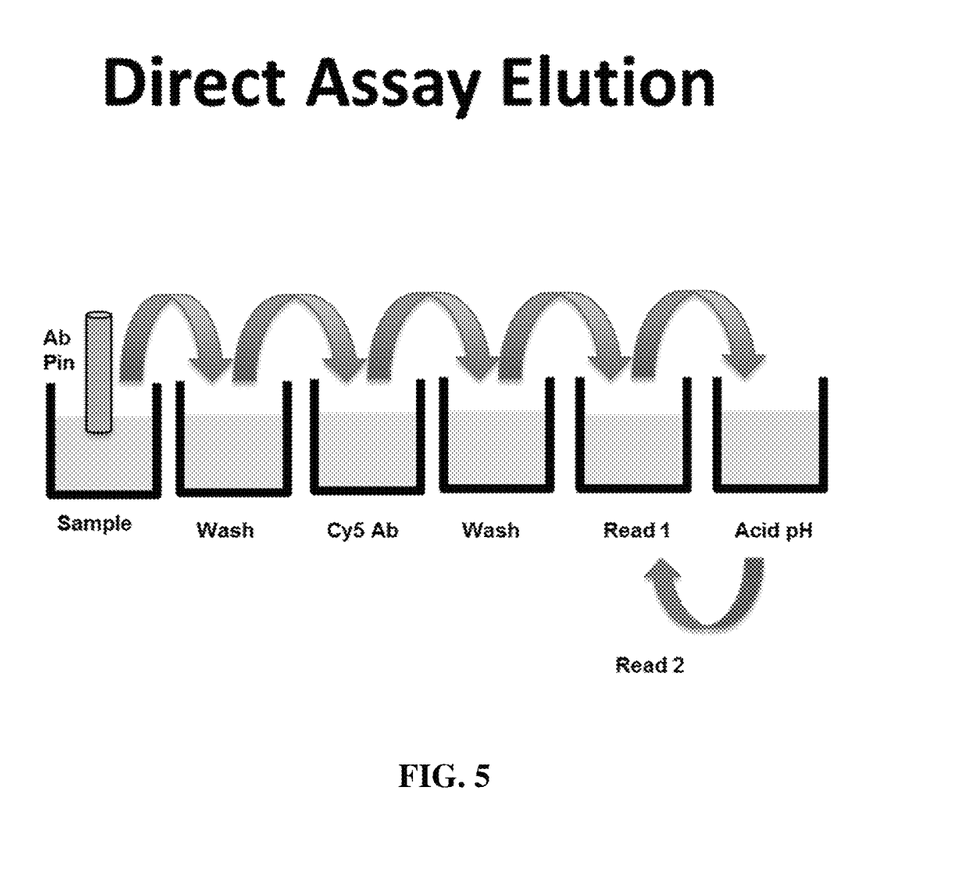
FIG. 5 illustrates a method of detecting an analyte in a liquid sample, using fluorescence-labeled antibody and acid elution protocols in a direct antibody binding assay. The fluorescent signal of eluted materials is calculated by subtracting a second fluorescent signal read on a probe from a first fluorescent signal read on the probe. Ab: antibody.

In one embodiment, the luminescent signal of eluted materials is calculated by subtracting a second luminescent signal on a probe from a first luminescent signal on the probe. The method comprises the steps of: (a) dipping a probe tip into a sample vessel containing a sample solution to bind an analyte, if present, to the first antibody on the probe tip, wherein the probe having a first antibody against the analyte immobilized on the tip of the probe; (b) dipping the probe tip into a reagent vessel containing a reagent solution comprising a second antibody against the analyte, conjugated with luminescent labels to form an immunocomplex among the analyte, the first antibody, and the second antibody on the probe tip; (c) dipping the probe tip into a washing vessel containing a wash solution; (d) dipping the probe tip in a read vessel and measuring a first luminescent signal of materials bound on the probe tip; (e) dipping the probe tip into an elution solution having pH 2.0-5.0 to elute materials from the probe tip; (f) dipping the probe tip in the read vessel and measuring a second luminescent signal of materials bound on the probe tip; (g) calculating the luminescent signal of eluted materials by subtracting the second luminescent signal from the first luminescent signal, and determining the analyte amount. The method is illustrated in FIG. 5.

In the present method, the probe is immobilized with an antibody against the analyte, before the assay. Methods to immobilize a first antibody to a solid phase (the sensing surface of the probe tip) are common in immunochemistry and involve formation of covalent, hydrophobic or electrostatic bonds between the solid phase and antibody. The first antibody, also called capture antibody for its ability to capture the analyte, can be directly immobilized on the sensing surface by various methods known in the art. For example, a first antibody can be directly immobilized either by adsorption to the solid surface or by covalently binding to aminopropylsilane coated on the solid surface. Alternatively, the first antibody can be indirectly immobilized on the sensing surface through a binding pair. For example, the first antibody can be labeled with biotin by known techniques (see Wilchek and Bayer, (1988) Anal. Biochem. 171:1-32), and then be indirectly immobilized on the sensing surface coated with streptavidin. Biotin and streptavidin are a preferred binding pair due to their strong binding affinity, which does not dissociate during the regeneration steps of the present method. The capture antibody immobilized on the sensing surface must be able to survive the denaturation condition when the probe sensing surface is regenerated to remove the immunocomplex bound to the sensing surface after the immunoreaction. The capture antibody immobilized on the sensing surface must not lose a significant amount of activity or significantly disassociate from the solid phase so that the immunoassay performance is compromised.

In one embodiment, the present method uses a probe that has a small tip for binding an analyte. The tip has a smaller surface area with a diameter ≤5 mm, preferably ≤2 mm or ≤1 mm. The small surface of the probe tip endows it with several advantages. In a solid phase immunoassays, having a small surface area is advantageous because it has less non-specific binding and thus produces a lower background signal. Further, the reagent or sample carry over on the probe tip is extremely small due to the small surface area of the tip. This feature makes the probe tip easy to wash, and causes negligible contamination in the wash solution since the wash solution has a larger volume.

In step (a) of the method, the probe tip is dipped into a sample vessel (or a sample chamber or a sample well), and incubated for a period of time, to bind the analyte to the first antibody on the probe tip. The incubation time preferably is a short period of time (≤5 or 10 minutes), for example, is 5 seconds to 5 minutes, 10 seconds to 2 minutes, 30 seconds to 2 minutes, 10 seconds to 1 minute, or 30 seconds to 1 minute.

After step (a), the probe is optionally washed 1-5 times, preferably 1-3 times in a wash vessel (or a wash chamber or a wash well) containing an aqueous wash solution. This washing step may not be required if the carried-over solution is minimal. The wash solution typically contains buffer and a surfactant such as Tween 20.

In step (b) of the method, the probe tip is dipped into a reagent vessel (or a reagent chamber or a reagent sell) to bind the reagent to the analyte on the probe tip. The incubation time preferably is a short period of time (≤5 or 10 minutes), for example, is 5 seconds to 5 minutes, 10 seconds to 2 minutes, 30 seconds to 2 minutes, 10 seconds to 1 minute, or 30 seconds to 1 minute. The reagent solution comprises a luminescent labelled second antibody (a signal antibody).

Any suitable luminescent label such as fluorescent label or chemiluminescent can be used in this method. The fluorescent label useful for this invention has a molecular weight of <5,000, preferably <2,000, such as 500-2000 or 100-2000 Daltons. In one embodiment, the fluorescent dye is selected from the group consisting of: cyanine, coumarin, xanthene and a derivative thereof. For example, the fluorescent dye is Cy5 (molecule weight MW 792), Alexa Fluor 647, DyLight 350 (MW 874), DyLight 405 (MW793), DyLight 488 (MW 71011), DyLight 550 (MW 982), DyLight 594 (MW 1078), DyLight 633 (MW 1066), DyLight 650 (MW 1008), DyLight 680 (MW 950), DyLight 755 (MW 1092), DyLight 800 (MW 1050), an Oyster fluorescent dye, IRDye, or organic compounds comprising multiple rings chelated with a rare earth metal such as a lanthanide (Eu, Th, Sm, or Dy).

One example of a fluorescent label is an arylsulfonate cyanine fluorescent dye as described in Mujumdar et al. (1993) *Bioconjugate Chemistry*, 4:105-111; Southwick et al. (1990) *Cytometry*, 11:418-430; and U.S. Pat. No. 5,268,486. Cy5 is a preferred arylsulfonate cyanine fluorescent dye, because it has a high extinction coefficient and good quantum yield; it also has fluorescent emission spectra in a range (500 nm to 750 nm) outside of the auto-fluorescence wavelengths of most biological materials and plastics. In addition, Cy5 has a good solubility in water, and has low non-specific binding characteristics.

Other luminescent labels may replace fluorescent labels and be used in this invention. For example, luminescent label can be a chemiluminescent marker such as luminol (MW 177) and an acridinium ester (9[[4-[3-[(2,5-dioxo-1-pyrrolidinyl)oxy]-3-oxopropyl]phenoxy]carbonyl]-10-methyl-acridinium trifluoromethane sulfonate, MW 632). Luminescent label can also be an electrochemiluminescent marker such as ruthenium(II)tris-bipyridine (MW 1057).

A luminescent label can covalently bind to a second antibody through a variety of moieties, including disulfide, hydroxyphenyl, amino, carboxyl, indole, or other functional groups, using conventional conjugation chemistry as described in the scientific and patent literature. Exemplary techniques for binding arylsulfonate cyanine fluorescent dye labels to antibodies and other proteins are described in U.S. Pat. Nos. 5,268,486; 5,650,334; the contents of which are in incorporated herein by reference. Techniques for linking a preferred Cy5 fluorescent label to antibodies are described in a technical bulletin identified as Cat. No. A25000, published by Biological Detection Systems, Inc., Pittsburgh, Pa.

In Step (c), the probe is washed 1-5 times, preferably 1-3 times in a first wash vessel containing a wash solution. The wash solution typically contains buffer and a surfactant such as Tween 20.

In step (d), the probe is moved to a read vessel and the luminescent signal of the immunocomplex bound on the probe tip is detected by the luminescent detection system as described above (e.g., see FIG. 3), where the light source and the detector are mounted at the same side (the proximal side) of the sensing surface of the probe. Alternatively, the luminescent signal can be detected by other suitable luminescent detection systems. A read vessel contains an aqueous solution such as water. A wash vessel that is used to wash the probe after sample incubation can also be used as a read vessel.

In step (e), the immunocomplex bound on the probe is eluted by employing a denaturing condition that dissociates the materials such as immune complexes bound to the probe. In general, an acid or an acidic buffer having pH about 1.5 to about 5.5 or about 2.0 to 5.5 is effective to elute the immunocomplex bound on the probe. For example, hydrochloric acid, sulfuric acid, nitric acid, acetic acid or acidic buffers can be used for elution. Depending on the analyte and the assay, an optimal pH can be about pH 2.0-3.0, 3.0-4.0, 3.5-4.5, or 4.0-5.0.

After the elution step (e), the probe tip is dipped in the read vessel and its luminescent signal (a second luminescent signal) is measured in step (f).

In step (g), the luminescent signal of eluted materials is calculated by subtracting the second luminescent signal from the first luminescent signal, and the analyte amount is determined by quantitating the luminescent signal of the eluted materials against a calibration curve (a standard curve). The calibration curve is typically pre-established before assaying the samples.

Prior to the sample binding in step (a), the luminescent signal of a probe tip is optionally pre-read by the same luminescent detection system in a read vessel. The read vessel contains an aqueous solution such as water or a buffer. Pre-read establishes a baseline of any potential background luminescent of the probe tip.

In the above steps, the reaction can be accelerated by agitating or mixing the solution in the vessel. For example, a flow such as a lateral flow or an orbital flow of the solution across the probe tip can be induced in one or more reaction vessels, including sample vessel, reagent vessel, wash vessels, and/or elution vessel, to accelerates the binding reactions, dissociation. For example, the reaction vessels can be mounted on an orbital shaker and the orbital shaker is rotated at a speed at least 50 rpm, preferably at least 200 rpm or at least 500 rpm, such as 50-200 or 500-1,500 rpm. Additionally, the probe tip can be moved up and down and perpendicular to the plane of the orbital flow, at a speed of 0.01 to 10 mm/second, in order to induce additional mixing of the solution above and below the probe tip.

In an alternative embodiment of the direct antibody binding assay, the analyte amount is determined directly from the luminescent signal of eluted materials in a liquid phase using a different optic system. The method comprises the steps of: (a) dipping a probe tip into a sample vessel containing a sample solution to bind an analyte, if present, to the first antibody on the probe tip, wherein the probe having a first antibody against the analyte immobilized on the tip of the probe; (b) dipping the probe tip into a reagent vessel containing a reagent solution comprising a second antibody against the analyte conjugated with luminescent labels to form an immunocomplex among the analyte, the first antibody, and the second antibody on the probe tip; (c) dipping the probe tip into a washing vessel containing a wash solution; (d) dipping the probe tip into an elution vessel containing an elution solution having pH 2.0-5.0 to elute materials from the probe tip; (e) removing the probe tip from the elution vessel; (f) measuring the luminescent signal of eluted materials in the elution vessel; and determining the analyte amount.

In this alternative embodiment, steps (a)-(e) are the same as those described above in the first embodiment. After step (e), the probe is removed and the probe is no longer in the measurement step. The luminescent signal of eluted materials is measured directly from the liquid phase in the elution vessel using a luminescent detection system as described above (e.g., see FIG. 4).

Amplification Assay

In a second aspect, the present invention is directed to a method of detecting an analyte in a liquid sample, using a binding pair and a high molecular weight polymer having multiple luminescent labels.

Figure 6:
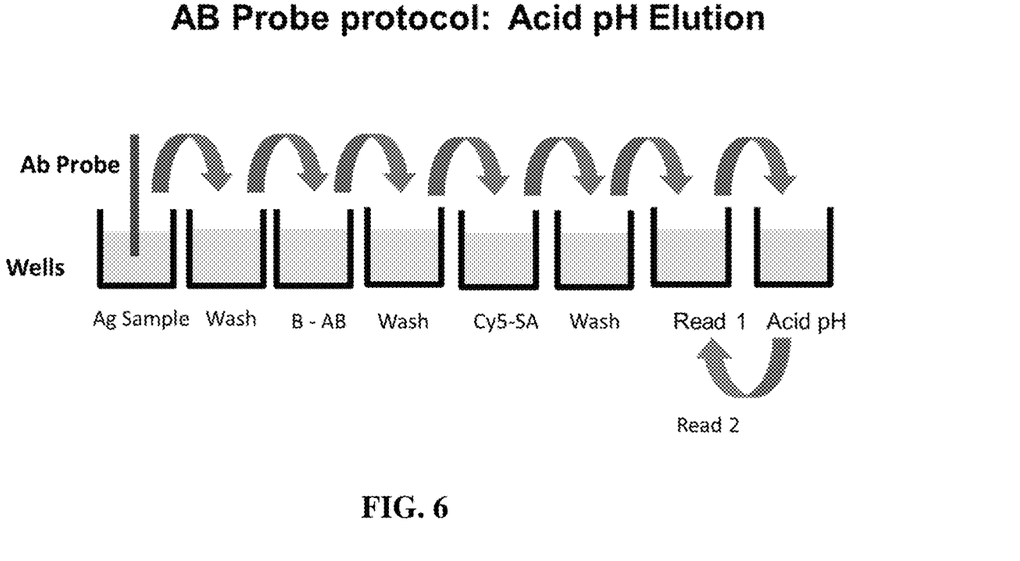
FIG. 6 illustrates a method of detecting an analyte in a liquid sample, using a binding pair and a high molecular weight polymer having multiple fluorescent labels in an amplification assay. Ag: antigen; AB: antibody; B-AB: biotin-Antibody; Cy5-SA: Cy5-Streptavidin.

In a first embodiment, the luminescent signal of eluted materials is calculated by subtracting a second luminescent signal read on a probe from a first luminescent signal read on the probe. The method comprises the steps in the order of: (a) dipping a probe tip into a sample vessel containing a sample solution to bind an analyte, if present, to the first antibody on the probe tip, wherein the probe having a first antibody against the analyte immobilized on the tip of the probe; (b) dipping the probe tip into a reagent vessel containing a reagent solution comprising a reagent of a second antibody against the analyte conjugated with a first member of a binding pair to bind the reagent to the analyte; (c) dipping the probe tip into a first wash vessel containing a first wash solution to wash the probe tip; (d) dipping the probe tip into an amplification vessel containing an amplification solution comprising a crosslinked polysaccharide having a molecular weight of at least 1 million Daltons and conjugated with at least 5 molecules of second member of the binding pair and at least 25 luminescent labels, to form an immunocomplex of the analyte, the first antibody, the second antibody, and the first and the second members of the binding pair on the probe tip; (e) dipping the probe tip into a second washing vessel containing a second wash solution; (f) dipping the probe tip in a read vessel and measuring a first luminescent signal of materials bound on the probe tip; (g) dipping the probe tip into an elution solution having pH 2.0-5.0 to elute materials from the probe tip; (h) dipping the probe tip in the read vessel and measuring a second luminescent signal of materials bound on the probe tip; (i) calculating the luminescent signal of eluted materials by subtracting the second luminescent signal from the first luminescent signal, and determining the analyte amount. This assay protocol is illustrated in FIG. 6.

Figure 7:
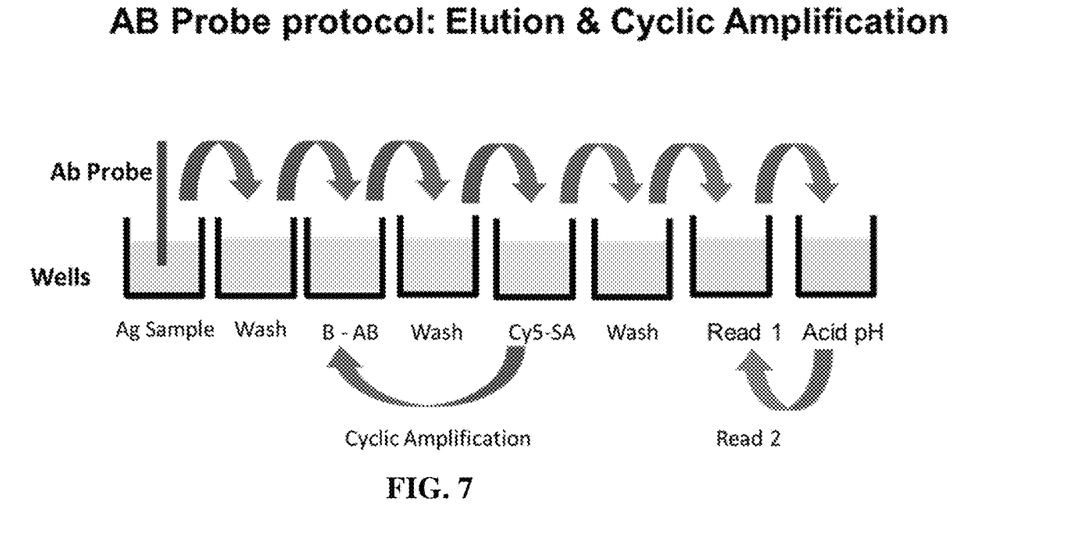

The second embodiment is similar to the first embodiment, except it has additional cyclic amplification steps to improve sensitivity. The method of the second embodiment further comprises a step (f') after step (f) and before (g). Step (f') is repeating steps (b) to (e) 1-10 times. This assay protocol is illustrated in FIG. 7.

The details of each step of amplification assay is similar to those described above for the direct antibody binding assay except steps (b) and (d), which use a binding pair and an amplification polymer.

The binding pair is typically a hapten and its antibody, a ligand and its receptor, complementary strands of nucleic acids, or lectin and carbohydrates. For example, the binding pair is biotin and streptavidin, biotin and avidin, biotin and neutravidin, fluorescein and anti-fluorescein, digioxigenin and anti-digioxigenin, and DNP (dinitrophenol) and anti-DNP. For example, the first member of the binding pair is biotin and the second member of the binding pair is streptavidin.

The amplification solution comprises a polymer conjugated with at least 5 molecules of second member of the binding pair and at least 25 luminescent labels. The polymer has a molecular weight of at least 500,000, preferably 1 million Daltons. The polymer can be a polysaccharide (e.g. FICOLL® or dextran), a polynucleotide, a dendrimer, a polyol, or polyethylene glycol. The polymer is preferably branched to have a 2- or 3-dimensional structure. The polymer preferably comprises 5-50 or 5-100 binding molecules and 25-100 or 25-500 luminescent molecules.

When the binding molecule is a polypeptide or protein, the luminescent label can covalently bind to it through a variety of moieties, including disulfide, hydroxyphenyl, amino, carboxyl, indole, or other functional groups, using conventional conjugation chemistry as described in the scientific and patent literature.

Step (f') is cycling amplification by repeating steps (c)-(f) 1-10 times, preferably 1-5 times or 2-3 times. Each cycle consists of placing the probe back to the same reagent vessel, the same first wash vessel, the same amplification vessel, and the same second wash vessel.

For cyclic amplification, a probe with a small surface area is preferred because it has a small binding capacity. Consequently, when the probe tip is immersed in a reagent solution, the binding of the reagent does not consume a significant amount of the reagent. The reagent concentration is effectively unchanged. Negligible contamination of the wash solution and small consumption of the reagents enable the reagents and the wash solution to be re-used many times, for example, 3-10 times.

In an alternative embodiment of the amplification assay, the analyte amount is determined directly from reading the luminescent signal of eluted materials in a liquid phase using a different optic system.

The alternative method comprises the steps in the order of: (a) dipping a probe tip into a sample vessel containing a sample solution to bind an analyte, if present, to the first antibody on the probe tip, wherein the probe having a first antibody against the analyte immobilized on the tip of the probe; (b) dipping the probe tip into a reagent vessel containing a reagent solution comprising a reagent of a second antibody against the analyte, conjugated with a first member of a binding pair to bind the reagent to the analyte; (c) dipping the probe tip into a first wash vessel containing a first wash solution to wash the probe tip; (d) dipping the probe tip into an amplification vessel containing an amplification solution comprising a crosslinked polysaccharide having a molecular weight of at least 1 million Daltons and conjugated with at least 5 molecules of second member of the binding pair and at least 25 luminescent labels, to form an immunocomplex of the analyte, the first antibody, the second antibody, and the first and the second members of the binding pair on the probe tip; (e) dipping the probe tip into a second washing vessel containing a second wash solution; (f) dipping the probe tip into an elution vessel containing an elution solution having pH 2.0-5.0 to elute materials from the probe tip; (g) removing the probe tip from the elution vessel; (h) measuring the luminescent signal of eluted materials in the elution vessel; and determining the analyte amount.

In this alternative embodiment, steps (a)-(f) are the same as those described above in the first embodiment. After step (f), the probe is removed and the probe is no longer in the measurement step. The luminescent signal of eluted materials is measured directly from the liquid phase in the elution vessel using a luminescent detection system as described above (e.g., see FIG. 4).

To improve the sensitivity, the above method can further comprise a step (e') after step (e) and before step (f). The cyclic amplification step (e') repeats steps (b) to (e) 1-10 times.

The invention is illustrated further by the following examples that are not to be construed as limiting the invention in scope to the specific procedures described in them.

EXAMPLES

Examples 1-12 illustrates one embodiment of the invention, i.e., elution assays with cyclic amplification using a binding pair and crosslinked polymer highly labelled with a fluorescent dye. Example 13 illustrates another embodiment of the invention, i.e., elution assay using antibody directly labeled with a fluorescent dye.

Example 1: Preparation of Probe Having Immobilized First Antibody (Anti-Troponin)

Quartz probes, 1 mm diameter and 2 cm in length, were coated with aminopropylsilane using a chemical vapor deposition process (Yield Engineering Systems, 1224P) following manufacturer's protocol. The probe tip was then immersed in a solution of murine monoclonal anti-fluorescein (BiosPacific), 10 µg/ml in PBS (phosphate-buffered saline) at pH 7.4. After allowing the antibody to adsorb to the probe for 20 minutes, the probe tip was washed in PBS. Theses antibody-coated probes were used in Examples 1-12.

Capture antibodies for troponin I (TnI), IL-6, obtained from BiosPacific, and procalcitonin (Hytest) were labeled with fluorescein by standard methods. Typically, there were about 4 fluorescein substitutions per antibody. Anti-fluorescein coated probes were immersed in fluorescein labeled capture antibody solution, 5 µg/ml, for 5 minutes followed by washing in PBS.

Example 2. Preparation of Crosslinked FICOLL® 400-SPDP

To 2 ml of FICOLL® 400 (Sigma/Aldrich) that was aminated to contain 88 amines per Ficoll 400 kD (Skold Technology) at 20 mg/ml in PBS was added 10 µL of SPDP (succinimydyl 6-[3-[2-pyridyldithio]-proprionamido] hexanoate, Invitrogen) at 50 mg/ml in DMF (N,N-Dimethylformamide). The SPDP to Ficoll molecular coupling ratio (MCR) was 15. The mixture reacted for 1 hour at room temperature and followed by dialysis. Thiol incorporation was estimated to be 5.5 per Ficoll 400 kD by standard methods.

Example 3. Preparation of Cy5-Streptavidin

32 µL of Cy 5-NHS (GE Healthcare) at 5 mg/ml in DMF reacted with 1 ml of streptavidin (Scripps Labs) at 2.4 mg/ml in 0.1 M sodium carbonate buffer pH 9.5 for 40 minutes at 30° C. Applying the mixture to a PD 10 column (Pharmacia) removed unconjugated Cy 5. Spectral analysis indicated 2.8 Cy 5 linked per streptavidin molecule.

Example 4. Preparation of Cy5-Streptavidin-Crosslinked FICOLL®

5.8 µL of SMCC (succinimidyl 4-[N-malemidomethyl] cyclohexan-1-carboxylate) Pierce Chemical) at 10 mg/ml in DMF reacted with 2 mg Cy5-streptavidin (Example 2) in 1 ml PBS pH 7.4 for 1 hour at room temperature. Applying the mixture to a PD 10 column removed unbound SMCC.

The thiols on crosslinked FICOLL® 400-SPDP (Example 1) were deprotected by adding 30 µL DTT at 38 mg/ml to 1 mg crosslinked FICOLL® 400-SPDP in 1 ml PBS and reacting for 1 hour at room temperature, followed by a PD 10 column to purify the crosslinked FICOLL®400-SH.

The Cy5-streptavidin-SMCC was mixed with crosslinked FICOLL® 400-SH and reacted overnight at room temperature. 10 µL NEM (Aldrich) at 12.5 mg/ml was then added and reacted for ½ hour at room temperature. The conjugate was then purified on a Sepharose 4B CL column. It was estimated that the conjugate carried about 20 to 30 streptavidins per FICOLL® (2 million Daltons), and 2-3 Cy5s per streptavidin.

Example 5: Cyclic Amplification Elution Assay Protocol and Reagents

This example follows the general cyclic amplification protocol shown in FIG. 7. Table 1 shows the assay protocol employed for troponin (TnI), Interleukin-6 (IL-6) and procalcitonin (PCT). 20 µL of sample were mixed with assay buffer (100 µL it PBS, 5 mg/ml BSA, 0.05% Tween 20, pH 7.4) and probe was dipped in. Wash buffer was 200 µL PBS, 0.05% Tween 20. Antibodies for TnI (Hytest), IL-6 (BiosPacific), and PCT (Hytest) were biotinylated (B-ab) with a standard method and used in the assay at about 5 µg/ml in 120 µL. The Cy5-steptavidin-FICOLL® was used at about 10 µg/ml in 120 µL.

TABLE 1

| Step | Time (sec) | RPM (Rotation per minute) |
|---|---|---|
| Pre-Read | | |
| Sample incubation | 600 | 1200 |
| 2 x wash | 15 | 1200 |
| Biotin-Antibody (B-Ab) | 60 | 1200 |
| 2 x wash | 15 | 1200 |
| Cy5-Streptavidin-FICOLL ® | 30 | 1200 |
| 2 x wash | 15 | 1200 |
| B-Ab (2nd cycle) | 15 | 1200 |
| 2 x wash | 15 | 1200 |
| Cy5-Streptavidin-FICOLL ® | 15 | 1200 |
| 2 x wash | 15 | 1200 |
| Read 1 | / | / |
| Acid Elution | 45 | 1200 |
| PBS | 30 | 1200 |
| Read 2 | / | / |

Example 6: Effects of Elution pH from 2.0-4.0

Example 6 illustrates the effects for acidic buffers on elution, following the protocols of Example 5. Different acid buffers were as follows: 10 mM glycine/HCl, pH 2.0; 10 mM glycine/HCl pH 3.0; 100 mM Na acetate/acetic acid pH 4.0.

The results are summarized in Tables 2-4. Read 1 is the fluorescence reading after acid elution. "Elution" is the fluorescence reading of Read 2 subtracted from Read 1, for an indirect estimate of the amount of fluorescent materials eluted from the probe. S=fluorescent signal, B=background fluorescent signal. S/B represents the ratio of specific signal to non-specific background signal. The improvement of S/B, particularly at low analyte level, improves the detection level.

TABLE 2

PH 2

| | Probe fluorescent Signal (v) | | |
|---|---|---|---|
| TnI | Read 1 (S/B) | Read 2 After Acid (S) | Elution (S/B) Read 1-Read 2 |
| 100 pg/ml | 732 (7.9) | 117 | 615 (14) |
| 10 pg/ml | 166 (1.8) | 65 | 101 (2.4) |
| 0 | 93 | 50 | 43 |

TABLE 3

PH 3

| | Probe fluorescent Signal (v) | | |
|---|---|---|---|
| TnI | Read 1 (S/B) | Read 2 After Acid (S) | Elution (S/B) Read 1-Read 2 |
| 100 pg/ml | 624 (7.7) | 88 | 536 (13) |
| 10 pg/ml | 181 (2.2) | 76 | 105 (2.6) |
| 0 | 81 | 40 | 41 |

TABLE 4

PH 4

| | Probe fluorescent Signal (v) | | |
|---|---|---|---|
| TnI | Read 1 (S/B) | Read 2 After Acid (S) | Elution (S/B) Read 1-Read 2 |
| 100 pg/ml | 596 (8.4) | 159 | 437 (46) |
| 10 pg/ml | 132 (1.8) | 72 | 60 (6.0) |
| 0 | 71 | 61 | 10 |

The Results of Tables 2-4 show that the amount of elution increases as the pH is lowered from 4 to 2. Taking TnI signal and dividing by the negative (0) signal determines the signal to background ratio (S/B). The results show that the S/B of elution (6.0) was about three fold better than the S/B of Read 1 (1.8) at 10 pg/ml level at pH 4.0 elution. Also, the S/B of elution (6.0) at pH 4 was better than the S/B (2.4) of at pH 2 at 10 pg/ml level.

Example 7

Example 7 illustrates the effects for acidic buffers on elution from pH 4 to 5.5, following the protocols of Example 5. Different acid buffers were as follows: 100 mM Na acetate/acetic acid pH 4.0; 100 mM Na acetate/acetic acid pH 5.0; 100 mM Na acetate/acetic acid pH 5.5.

TABLE 5

PH 4

| | Probe fluorescent Signal (v) | | |
|---|---|---|---|
| TnI | Read 1 (S/B) | Read 2 After Acid (S) | Elution (S/B) Read 1-Read 2 |
| 100 pg/ml | 2044 (29) | 258 | 1786 (64) |
| 10 pg/ml | 290 (4) | 54 | 236 (8) |
| 0 | 70.5 | 43 | 28 |

TABLE 6

PH 5

| | Probe fluorescent Signal (v) | | |
|---|---|---|---|
| TnI | Read 1 (S/B) | Read 2 After Acid (S) | Elution (S/B) Read 1-Read 2 |
| 100 pg/ml | 1796 (29) | 1301 | 495 (35) |
| 10 pg/ml | 233 (4) | 150 | 83 (6) |
| 0 | 61 | 47 | 14 |

TABLE 7

PH 5.5

| | Probe fluorescent Signal (v) | | |
|---|---|---|---|
| TnI | Read 1 (S/B) | Read 2 After Acid (S) | Elution (S/B) Read 1-Read 2 |
| 100 pg/ml | 1802 (23) | 1147 | 655 (28) |
| 10 pg/ml | 249 (3) | 143 | 106 (5) |
| 0 | 79 | 56 | 23 |

Tables 5-7 show that the S/B of elution were all improved over the S/B of read 1. Around pH 4.0 appears to be optimal for S/B for cyclic amplification assay for troponin.

Example 8: Limit of Detection for Troponin Assay

Limit of blank (LOB) is defined as mean blank+1.645×(SD blank)

Limit of detection (LOD) is defined as LOB+1.645×(SD blank)

SD is standard deviation.

(David et al., Clin. Biochem. Rev. 29: S49-52)

Following the elution protocol of troponin with pH 4.0 acid treatment of Example 5, LOD was determined by Read 1 (one read only, no acid elution) and Read 2 (elution assay with acid elution). LOD was 2.9 pg/mL by read 1, and was improved to 1.3 pg/mL by elution assay.

Example 9: Detection Troponin in Normal Samples

Following the elution protocol of troponin of Example 5 at pH 4, 39 heparin plasma samples from 39 apparently normal individuals were measured for troponin level by direct assay (Read 1, no acid elution) and elution assay (Read 2, with acid elution). The troponin levels of 100% of the 39 normal samples were detected with elution assay, while only 46% were detected with Read 1.

The results show that the benefits of the elution assay of this invention apply to detecting TnI within the normal range.

Example 10: HsTnI Designation

Following the elution protocol of troponin of Example 8, 611 normal serum samples were detected for troponin levels.

The elution protocol detected 91% in the 611 normal serum samples tested, which falls in the $2^{nd}$ generation hsTnI designation. The $99^{th}$ percentile was 36 pg/mL with a between run CV of 10%, which is acceptable according to TnI Designation Guideline (see FIG. 1).

Example 11: IL-6 Assay

IL-6 is another analyte requiring high sensitivity measurements. Table 8 shows data for IL-6 follows the protocols of Example 6, using pH 4.0 acid elution.

TABLE 8

| | Probe fluorescent Signal (v) | | |
|---|---|---|---|
| IL-6 | Read 1 (S/B) | Read 2 After Acid (S) | Elution (S/B) Read 1-Read 2 |
| 5000 pg/mL | 5819 (65.4) | 1684 | 4136 (133.4) |
| 2500 pg/mL | 3254 (36.6) | 526 | 2728 (88.0) |
| 500 pg/mL | 758 (8.5) | 100 | 659 (21.2) |
| 250 pg/mL | 426 (4.8) | 73 | 353 (11.4) |
| 50 pg/mL | 149 (1.7) | 56 | 93 (3.0) |
| 25 pg/mL | 108 (1.2) | 47 | 61 (2.0) |
| 0 | 89 (1.0) | 58 | 31 (1.0) |

The results in Table 8 shows that elution protocol generates about a 2 fold improvement in S/B ratio comparing with no elution, and the elution protocol detected 25 pg/mL level in IL-6 assay.

Example 12: Procalcitonin Assay, Alternative Optical Detection Configurations Table 9 shows the protocols of PCT assay, using pH 4.0 acid elution. Fluorescent signals were measured with an alternative optical detection configuration. The optics with a wide laser beam and numerical aperture of the collecting lens directly detect the eluted labeled antibody in fluid phase.

TABLE 9

| Step | Time (sec) | RPM (Rotation per minute) |
|---|---|---|
| Pre-Read | | |
| Sample incubation | 600 | 1200 |
| 2 × wash | 2 × 15 | 1200 |
| Biotin-Antibody (B-Ab) | 60 | 1200 |
| 2 × wash | 2 × 15 | 1200 |
| Cy5-Streptavidin-FICOLL ® | 30 | 1200 |
| 2 × wash | 2 × 15 | 1200 |
| B-Ab (2nd cycle) | 15 | 1200 |
| 2 × wash | 2 × 15 | 1200 |
| Cy5-Streptavidin-FICOLL ® | 15 | 1200 |
| 2 × wash | 2 × 15 | 1200 |
| Acid Elution | 45 | 1200 |
| PBS | 30 | 1200 |
| Read Eluted Materials in Liquid Phase | / | / |

Table 10 shows the dose-response results of the PCT assay.

TABLE 10

| PCT Concentration (ng/mL) | Fluorescent Signal (V) |
|---|---|
| 0 | 128 |
| 0.5 | 842 |
| 1.1 | 1687 |
| 2.3 | 3144 |
| 4.6 | 5721 |

Example 13. Direct Antibody Assay of C-Reactive Protein (CRP)

Example 13 illustrates another embodiment of the invention, i.e., elution assay using antibody directly labeled with a fluorescent dye, and without cyclic amplification. The assay follows the general protocols as shown in FIG. 5.

Preparation of Probe Having Immobilized First Antibody (Anti-CRP)

Quartz probes, 1 mm diameter and 2 cm in length, were coated with aminopropylsilane using a chemical vapor deposition process (Yield Engineering Systems, 1224P) following manufacturer's protocol. The probe tip was then immersed in a solution of streptavidin (Sigma-Aldrich), 10 µg/mL in phosphate-buffered saline pH 7.4 (PBS). After allowing the protein to adsorb to the probe for 5 minutes, the probe tip was washed in PBS. The probe tip was then immersed in a solution containing a biotin-labeled anti-CRP (Hytest) at 10 µg/mL in PBS. After 10 minutes, the probe tip was washed in PBS. The antibody was biotinylated by a standard method. The biotinylated antibody was designated as "capture antibody".

Preparation of CY5 Labeled Antibody

Anti-CRP (Hytest) at 3.2 mg/mL in 1 ml 0.1 M sodium carbonate pH 9.5 was mixed with 10.6 µL of Cy5-NHS (GE Healthcare) at 10 mg/ml in DMF and allowed to react for ½ hour at 30° C. The mixture was then purified on a PD 10 column (GE Healthcare). The Cy5 labeled antibody was designated as "signal antibody".

CRP Assay Protocol is shown in Table 11.

TABLE 11

| Step | Time (sec) | RPM |
|---|---|---|
| Pre-read | 0 | 1200 |
| CRP sample (120 μL) | 15 | 1200 |
| 3x wash (150 μL) | 3 × 7 | 1200 |
| Cy5-antiCRP (120 μL) | 15 | 1200 |
| 3x wash (150 μL) | 3 × 7 | 1200 |
| Read 1 | 0 | 0 |
| pH 2 | 10 | 1200 |
| Read 2 | 0 | 0 |

CRP Results are shown in Table 12.

TABLE 12

| | Probe fluorescent Signal (v) | | |
|---|---|---|---|
| CRP | Read 1 (S/B) | Read 2 After Acid (S) | Elution (S/B) Read 1-Read 2 |
| 10 mg/L | 484 (35) | 13 | 471 (471) |
| 3 mg/L | 171 (12) | 13 | 158 (158) |
| 1 mg/L | 83.5 (6) | 14 | 70 (70) |
| 0 | 14 | 13 | 1 |

The results show that elution protocol improves the signal to background ratio from 6 to 70 at the CRP level of 1 mg/L.

The invention, and the manner and process of making and using it, are now described in such full, clear, concise and exact terms as to enable any person skilled in the art to which it pertains, to make and use the same. It is to be understood that the foregoing describes preferred embodiments of the present invention and that modifications may be made therein without departing from the scope of the present invention as set forth in the claims. To particularly point out and distinctly claim the subject matter regarded as invention, the following claims conclude this specification.

What is claimed is:

1. A method of detecting an analyte in a liquid sample, comprising the steps of:
   (a) dipping a probe tip into a sample vessel containing a sample solution to bind an analyte, if present, to a first antibody on the probe tip, wherein the probe having the first antibody against the analyte immobilized on the tip of the probe;
   (b) dipping the probe tip into a reagent vessel containing a reagent solution comprising a second antibody against the analyte, conjugated with luminescent labels to form an immunocomplex among the analyte, the first antibody, and the second antibody on the probe tip;
   (c) dipping the probe tip into a washing vessel containing a wash solution;
   (d) dipping the probe tip in a read vessel and measuring a first luminescent signal of materials bound on the probe tip;
   (e) dipping the probe tip into an elution solution having pH 2.0-5.0 to elute materials from the probe tip;
   (f) dipping the probe tip in the read vessel and measuring a second luminescent signal of remaining materials bound on the probe tip after step (e);
   (g) calculating the luminescent signal of eluted materials by subtracting the second luminescent signal from the first luminescent signal, and determining the analyte amount.

2. The method according to claim 1, wherein the tip surface is ≤about 5 mm.

3. The method according to claim 1, wherein the luminescent label is a fluorescent label.

4. The method according to claim 3, wherein the fluorescent label is selected from the group consisting of: cyanine, coumarin, xanthene and a derivative thereof.

5. The method according to claim 4, wherein the fluorescent label is arylsulfonate cyanine.

6. The method according to claim 3, wherein the elution solution has pH of 2.0-3.0.

7. The method according to claim 3, wherein the elution solution has pH of 2.0-3.0.

8. The method according to claim 3, wherein the analyte is troponin I.

9. The method according to claim 3, wherein the tip surface is ≤about 2 mm.

10. The method according to claim 1, wherein the luminescent label is ruthenium(II)tris-bipyridine.

11. The method according to claim 1, wherein the elution solution has pH of 3.0-4.0.

12. The method according to claim 1, wherein the elution solution has pH of 3.0-4.0.

13. The method according to claim 1, wherein the analyte is troponin I.

14. The method according to claim 1, wherein the tip surface is ≤about 2 mm.

* * * * *